United States Patent [19]

Sano et al.

[11] Patent Number: 5,306,725
[45] Date of Patent: Apr. 26, 1994

[54] STABILIZED ISOTHIAZOLONE LIQUID FORMULATION

[75] Inventors: Yoichi Sano, Takatsuki; Katsuji Tsuji, Kyoto; Sakae Katayama, deceased, late of Nishinomiya, all of Japan, by Hirohiko Katayama, Executor

[73] Assignee: Katayama Chemical Inc., Osaka, Japan

[21] Appl. No.: 970,231

[22] Filed: Oct. 30, 1992

Related U.S. Application Data

[63] Continuation of Ser. No. 745,250, Aug. 14, 1991, abandoned.

[51] Int. Cl.⁵ ............... A01N 43/80; C07D 275/03
[52] U.S. Cl. ............................. 514/372; 548/213
[58] Field of Search ..................... 548/213; 514/372

[56] References Cited

U.S. PATENT DOCUMENTS 4,824,957  4/1989  Amick ........................... 548/213

FOREIGN PATENT DOCUMENTS 0349786  1/1990  European Pat. Off. .
2-85271  3/1990  Japan .

*Primary Examiner*—Joseph P. Brust
*Assistant Examiner*—Mary Susan H. Gabilan
*Attorney, Agent, or Firm*—Sandler Greenblum & Bernstein

[57] ABSTRACT

A stabilized isothiazolone liquid formulation including: an isothiazolone compound represented by the formula (I):

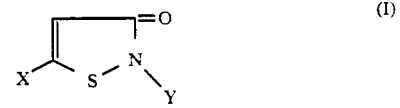

(where X represents a hydrogen atom or halogen atom, and Y represents a lower alkyl group), and a mixed solvent containing 50–99.9 wt. % of a glycol-type solvent and 50–0.1 wt. % of an amide-type compound represented by the formula (II):

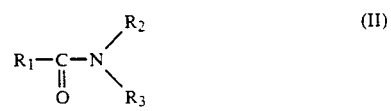

where $R_1$ represents a hydrogen atom or a lower alkyl group, $R_2$ and $R_3$ each represent a lower alkyl group, $R_1$ may bond to $R_2$ or $R_3$ to form a nitrogen-containing heterocycle), the compound of the formula (I) being dissolved in the mixed solvent of which amount is at least sufficient to dissolve the compound of the formula (I).

5 Claims, No Drawings

STABILIZED ISOTHIAZOLONE LIQUID FORMULATION

This application is a continuation of application Ser. No. 07/645,250, filed Aug. 14, 1991, now abandoned.

BACKGROUND OF THE INVENTION

1. Field of the Invention

The present invention relates to a stabilized isothiazolone formulation. More specifically, it relates to a highly stabilized liquid formulation containing an isothiazolin-3-one compound useful as a non-medicinal biocide, which is capable of inhibiting decomposition of the isothiazolin-3-one compound even stored for a long period of time at room temperature or above.

2. Description of the Prior Art

Isothiazolone compounds such as 5-chloro-2-methylisothiazolin-3-one and 2-methy-isothiazolin-3-one have so far been known as a non-medicinal blocidal, antiseptic or antifungal agents. They are, in particular, useful as antiseptic or antifungal agents for synthetic polymeric emulsions such as NBR latex, SBR latex and acrylic resin emulsion.

The isothiazolone compounds are highly water-soluble, and accordingly it is desired to use them in the form of an aqueous solution in view of their dispersion into systems to be treated. However, the active ingredient of the aqueous isothiazolone formulations is decomposed in a short period of time to result in a precipitate, and at the same time, the content of an isothiazolone compound in the formulation decreases. Therefore, a mere aqueous solution of the compound is extremely unstable as a formulation, and cannot be put into practical use at all.

In view of the above, there has been proposed an aqueous formulation imparted with stability by forming an isothiazolone compound as a complex with a metal salt, such as a calcium or magnesium salt, or further adding thereto a stabilizer such as magnesium nitrate, and then dissolving it in water or in an aqueous solvent (Japanese Patent Laid-Open No. 23968/1979, U.S. Pat. No. 3,870,795). There has also been proposed recently an organic solvent formulation not containing water nor a metal salt, or a remarkably reduced amount of the same, which is prepared by dissolving an isothiazolone compound in a particular organic solvent, such as glycol-type solvent (Japanese Unexamined Patent Publication Nos. 56174/1986, 212576/1986).

Further, Japanese Unexamined Patent Publication No. 85271/1990 suggests the dissolving of an isothiazolone compound in a single or mixed solvent of two or more solvents selected from the group of ethylene glycol monomethyl ether acetate, ethylene glycol dimethyl ether, propylene carbonate, dimethylformamide, and the like; however this document specifically discloses the stability of formulations each containing a single solvent of the above solvents in which an isothiazolone compound is dissolved.

However, if the conventional aqueous formulation containing a complex of isothiazolone compound with a metal salt or containing a metal salt stabilizer as described above is added as it is by an effective amount as an antiseptic or antifungal agent to a synthetic polymeric emulsion, there arises a problem that the emulsion phase is broken to cause phase separation or coagulation (so-called emulsion shock) due to the effect of polyvalent metal ions such as of calcium or magnesium ions contained in the formulation, resulting in decreased antiseptic or antifungal action of the isothiazolone compound.

Further, although the above organic solvent formulation does not cause emulsion shock, it cannot contain an isothiazolone compound at high concentration. In addition, the decomposition of the isothiazolin-3-one compound cannot be satisfactorily inhibited when the formulation is stored for a long period of time. For example, the above U.S. Pat. No. 3,870,795 teaches at column 4, lines 35-45 that a non-aqueous solution containing about 25% of 5-chloro-2-methyl-3-isothiazolone/2-methyl-3-isothiazolone (93:7) decomposed completely when allowed to stand at 50° C. for 28 days.

The present invention has been made in view of the foregoing situations, and it is an object thereof to provide an isothiazolone compound formulation, not containing the above polyvalent metal ions, which is excellent in long storage stability.

SUMMARY OF THE INVENTION

In view of the above, it is an object of the present invention to improve the stability of an organic solvent formulation of the above described isothiazolone compound. In particular, intensive research has been conducted on the improvement of a glycol-type solvent formulation which can be easily handled and is considered to have reduced adverse effects to an emulsion.

As a result, it has been unexpectedly found that addition of an amide-type compound represented by the following formula (II) to a solution of an isothiazolone compound in a glycol-type solvent enables a remarkable improvement in formulation stability. the fact to reach the present invention.

amide-type solvent. Its addition to an isothiazolone formulation has been considered as having the possibility of lowering the formulation stability because the amide-type compound (II) basically exhibits weak alkalinity; wherein, the isothiazolone compound represented by the formula (I) is stable in an acidic solution.

Thus, the present invention provides a stabilized isothiazolone liquid formulation comprising:

an isothiazolone compound represented by the formula (I):

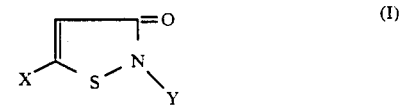

(where X represents a hydrogen atom or halogen atom, and Y represents a lower alkyl group), and a mixed solvent containing 50-99.9 wt. % of a glycol-type solvent and 50-0.1 wt. % of an amide-type compound represented by the formula (II):

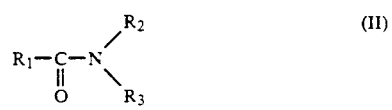

where $R_{10}$ represents a hydrogen atom or a lower alkyl group, $R_2$ and $R_3$ each represent a lower alkyl group, $R_1$ may bond to $R_2$ or $R_3$ to form a nitrogen containing heterocycle), the compound of the formula (I) being dissolved in the mixed solvent of which amount is at least sufficient to dissolve the compound of the formula (I).

DETAILED DESCRIPTION OF THE PREFERRED EMBODIMENTS

Examples of the halogen atom for the substituent X in the compound (I) used in the invention include chlorine, bromine and iodine, among which chlorine is preferable.

Examples of the lower alkyl group for the substituent Y include alkyl groups having 1-6 carbon atoms such as methyl, ethyl, propyl and butyl, among which a methyl group is preferable.

Typical examples of the compound (I) are 2-methyl-5-chloro-1,2-isothiazolin-3-one and 2-methyl-1,2-isothiazolin-3-one. These compounds of the formula (I) are in the form of powder at room temperature, and can be prepared in accordance with the synthesis method as described in Japanese Examined Patent Publication No. 12723/1971. These compounds are usually obtained as a mixture thereof and this. Such a mixture can also be suitably used in this invention.

As the glycol-type solvent for use in the invention, usable are various known polyols or polyol ether type liquid compounds, such as ethylene glycol, diethylene glycol, polyethylene glycol, propylene glycol, dipropylene glycol, tripropylene glycol, polypropylene glycol, 1,4-butanediol, 1,5-pentanediol, ethylene glycol monomethyl ether, ethylene glycol monoethyl ether, ethylene glycol monobutyl ether, diethylene glycol monomethyl ether, diethylene glycol monoethyl ether, tripropylene glycol monomethyl ether and the like. Among these, preferable are ethylene glycol, diethylene glycol, propylene glycol, dipropylene glycol and 1,4-butanediol.

Specific examples of the amide-type compound of the formula (II) include N,N-dimethylformamide, N,N-diethylformamide, N-methyl-N-ethylformamide, N-methyl-N-butylformamide, N-methyl-N-propylformamide, N-ethyl-N-propylformamide, N,N-dipropylformamide, N-propyl-N-butylformamide, N-ethyl-N-butylformamide, N,N-dibutylformamide, N,N-dimethylacetamide, N-methyl-N-ethyl-acetamide, N,N-diethylacetamide, N-methyl-N-propylacetamide, N-methyl-N-butylacetamide, N-ethyl-N-propylacetamide, N-ethyl-N-butylacetamide, N,N-dipropylacetamide, N-propyl-N-butylacetamide, N,N-dibutylacetamide, N-methyl-2-pyrrolidone, N-ethyl-2-pyrrolidone, N-propyl-2-pyrrolidone, N-butyl-2-pyrrolidone and the like. Among these, N,N-dimethylformamide, N,N-diethylformamide, N,N-dimethylacetamide and N-methyl-2-pyrrolidone are especially preferable.

The isothiazolone formulation of the invention is prepared by dissolving the compound (I) in the mixed solvent containing the above glycol-type solvent blended with the amide-type compound (II). The amount (by weight) of the amide-type compound to be blended with the glycol-type solvent should be the same as or less than that of the glycol-type solvent. It is suitable to set the amount of the amide-type compound in the mixed solvent to 0.1-50 wt. % (while the amount of glycol-type solvent to 99.9-50 wt. %), preferably 1-30 wt. %, and more preferably 2-20 wt. %. If it is less that 0.1 wt. %, satisfactory improvement on the formulation stability cannot be expected. As well, if it is more than 50 wt. %, little further improvement on the formulation stability is recognized, consequently, it is not well balanced with the amount of the amide-type compound to be added.

Although the amount of the compound (I) to be blended in the above mixed solvent is limited by the solubility of the compound (I) in the mixed solvent, it is preferably to include 0.1-30 wt. %, more preferably 0.5-20 wt. % for the formulation stability.

The isothiazolone liquid formulation thus prepared inhibits decomposition of the isothiazolone compound contained therein for the long period of time to remarkably improve the formulation stability, without using a metal salt stabilizer such as calcium salt and magnesium salt. Hence, even after long-term preservation or storage, the formulation of the invention exhibits a potent antiseptic or antifungal action originating from the isothiazolone compound contained therein.

It should be understood that if the formulation of the invention is diluted with water and stored, adding thereto a nonionic or anionic surface active agent, a nitrobromo-type compound such as 2-bromo-2-nitro-1,3-propanediol, 2,2-dibromo-2-nitroethanol, 2-bromo-2-nitro-1,3-diacetoxypropane and the like, or 2,2-dibromo-3-nitrylpropionamide further improves the storage stability thereof.

EXAMPLE

A mixture of 2-methyl-5-chloro-isothiazolin-3-one and 2-methyl-isothiazolin-3-one at 9:1 weight ratio (hereinafter simply referred to as MIT) as an isothiazolone compound was dissolved in various solvents as listed in Table 1 to obtain formulations of Examples 1–46 and Comparative Examples 1–15 (all of the numerals in Table 1 except Examples numbers represent weight part).

These formulation products were subjected to the following tests.

Storage Stability Test

Test method . . . Each of the formulations was placed in a glass vessel and allowed to stand at 50° C. The state of the formulation with elapse of time was observed, and the results were expressed as "◯" for the formulation showing no appearance change and no decomposition upon measurement by HPLC (High Performance Liquid Chromatography), as "Δ" for the formulation showing slight clouding in appearance and MIT decomposition rate of less than 5% as measured by HPLC, and as "X" for the formulation showing a great amount of deposited crystals in appearance and decomposition rate of more than 5%.

It is estimated from the test results for long years that the stability for 2 months at 50° C. in this test is substantially equivalent to the stability for 4 months at 40° C. and to the stability for more than one year at room temperature.

The results of this test are included in Table 1.

In the table, abbreviations indicate the following compounds.

| Abbreviation | Compound Name |
| --- | --- |
| DMF | N,N-dimethylformamide |
| DEF | N,N-diethylformamide |
| DMA | N,N-dimethylacetamide |
| MP | N-methyl-2-pyrrolidone |
| EG | Ethylene glycol |
| DEG | Diethylene glycol |
| PEG-200 | Polyethylene glycol (average molecular weight 200) |

| Abbreviation | Compound Name |
|---|---|
| PG | Propylene glycol |
| DPG | Dipropylene glycol |
| TPG | Tripropylene glycol |
| MDG | Diethylene glycol monomethyl ether |
| MEG | Ethylene glycol monomethyl ether |
| EDG | Diethylene glycol monoethyl ether |
| TPM | Tripropylene glycol monomethyl ether |

TABLE 1

| | No. | MIT | glycol-type solvent | | Compound (II) | | storage stability at 50° C. (day) | | | | | |
|---|---|---|---|---|---|---|---|---|---|---|---|---|
| | | | | | | | 7 | 14 | 21 | 30 | 45 | 60 |
| Example | 1 | 5.0 | EG | 94.9 | DMF | 0.1 | ○ | ○ | ○ | △ | X | X |
| | 2 | | " | 94.5 | " | 0.5 | ○ | ○ | ○ | ○ | △ | X |
| | 3 | | " | 94 | " | 1 | ○ | ○ | ○ | ○ | ○ | △ |
| | 4 | | " | 93 | " | 2 | ○ | ○ | ○ | ○ | ○ | ○ |
| | 5 | | " | 90 | " | 5 | ○ | ○ | ○ | ○ | ○ | ○ |
| | 6 | | " | 75 | " | 20 | ○ | ○ | ○ | ○ | ○ | ○ |
| | 7 | | " | 65 | " | 30 | ○ | ○ | ○ | ○ | ○ | ○ |
| | 8 | | " | 50 | " | 45 | ○ | ○ | ○ | ○ | ○ | ○ |
| | 9 | | EG | 90 | DEF | 5 | ○ | ○ | ○ | ○ | ○ | ○ |
| | 10 | | " | 90 | DMA | 5 | ○ | ○ | ○ | ○ | ○ | ○ |
| | 11 | | " | 90 | MP | 5 | ○ | ○ | ○ | ○ | ○ | △ |
| | 12 | | DEG | 90 | DMF | 5 | ○ | ○ | ○ | ○ | ○ | ○ |
| | 13 | | PEG-200 | 90 | " | 5 | ○ | ○ | ○ | ○ | ○ | ○ |
| | 14 | | PG | 90 | " | 5 | ○ | ○ | ○ | ○ | ○ | ○ |
| | 15 | | DPG | 90 | " | 5 | ○ | ○ | ○ | ○ | ○ | ○ |
| | 16 | | TPG | 90 | " | 5 | ○ | ○ | ○ | ○ | ○ | ○ |
| | 17 | | 1,4-butanediol | 90 | " | 5 | ○ | ○ | ○ | ○ | ○ | ○ |
| | 18 | | 1,5-pentanediol | 90 | " | 5 | ○ | ○ | ○ | ○ | ○ | ○ |
| | 19 | | MEG | 90 | " | 5 | ○ | ○ | ○ | ○ | ○ | ○ |
| | 20 | | MDG | 90 | " | 5 | ○ | ○ | ○ | ○ | ○ | ○ |
| | 21 | | EDG | 90 | " | 5 | ○ | ○ | ○ | ○ | ○ | ○ |
| | 22 | | TPM | 90 | " | 5 | ○ | ○ | ○ | ○ | ○ | ○ |
| | 23 | 0.5 | EG | 99.4 | DMF | 0.1 | ○ | ○ | ○ | ○ | X | X |
| | 24 | | EG | 99.0 | " | 0.5 | ○ | ○ | ○ | ○ | ○ | X |
| | 25 | | " | 98.5 | " | 1 | ○ | ○ | ○ | ○ | ○ | ○ |
| | 26 | | " | 94.5 | " | 5 | ○ | ○ | ○ | ○ | ○ | ○ |
| | 27 | | " | 79.5 | " | 20 | ○ | ○ | ○ | ○ | ○ | ○ |
| | 28 | 15 | EG | 84.9 | DMF | 0.1 | ○ | ○ | ○ | △ | X | X |
| | 29 | | " | 84.5 | " | 0.5 | ○ | ○ | ○ | ○ | △ | X |
| | 30 | | " | 84 | " | 1 | ○ | ○ | ○ | ○ | ○ | △ |
| | 31 | | " | 83 | " | 2 | ○ | ○ | ○ | ○ | ○ | ○ |
| | 32 | | " | 80 | " | 5 | ○ | ○ | ○ | ○ | ○ | ○ |
| | 33 | | " | 65 | " | 20 | ○ | ○ | ○ | ○ | ○ | ○ |
| | 34 | 30 | EG | 69.9 | DMF | 0.1 | ○ | ○ | ○ | X | | |
| | 35 | | " | 69.5 | " | 0.5 | ○ | ○ | ○ | △ | X | |
| | 36 | | " | 69 | " | 1 | ○ | ○ | ○ | ○ | △ | X |
| | 37 | | " | 68 | " | 2 | ○ | ○ | ○ | ○ | ○ | ○ |
| | 38 | | " | 65 | " | 5 | ○ | ○ | ○ | ○ | ○ | ○ |
| | 39 | | " | 50 | " | 20 | ○ | ○ | ○ | ○ | ○ | ○ |
| | 40 | 30 | PG | 69 | DMF | 1 | ○ | ○ | ○ | ○ | ○ | ○ |
| | 41 | | DPG | 69 | " | 1 | ○ | ○ | ○ | ○ | ○ | ○ |
| | 42 | | 1,4-butanediol | 69 | " | 1 | ○ | ○ | ○ | ○ | ○ | ○ |
| | 43 | | DEG | 69 | " | 1 | ○ | ○ | ○ | ○ | ○ | ○ |
| | 44 | 15 | EG | 84 | DEF | 1 | ○ | ○ | ○ | ○ | ○ | △ |
| | 45 | | " | 84 | DMA | 1 | ○ | ○ | ○ | ○ | ○ | △ |
| | 46 | | " | 84 | MP | 1 | ○ | ○ | ○ | ○ | △ | X |
| | | | solvent | | | | | | | | | |
| Comparative Example | 1 | 5 | EG | 95 | | | ○ | ○ | X | X | X | X |
| | 2 | 5 | DEG | " | | | ○ | ○ | X | X | X | X |
| | 3 | 5 | PEG-200 | " | | | ○ | ○ | X | X | X | X |
| | 4 | 5 | PG | " | | | ○ | ○ | X | X | X | X |
| | 5 | 5 | DPG | " | | | ○ | ○ | X | X | X | X |
| | 6 | 5 | TPG | " | | | ○ | ○ | X | X | X | X |
| | 7 | 5 | 1,4-butanediol | " | | | ○ | ○ | X | X | X | X |
| | 8 | 5 | 1,5-pentanediol | " | | | ○ | ○ | X | X | X | X |
| | 9 | 5 | 2,3-pentanediol | " | | | ○ | ○ | X | X | X | X |
| | 10 | 5 | MEG | " | | | ○ | ○ | X | X | X | X |
| | 11 | 5 | MDG | " | | | ○ | ○ | X | X | X | X |
| | 12 | 5 | EDG | " | | | ○ | ○ | X | X | X | X |
| | 13 | 5 | TPM | " | | | ○ | ○ | X | X | X | X |
| | 14 | 5 | Acetone | " | | | ○ | X | X | X | X | X |
| | 15 | 5 | Acetone + | 85 | | | ○ | X | X | X | X | X |

TABLE 1-continued

| No. | MIT | | storage stability at 50° C. (day) | | | | | |
|---|---|---|---|---|---|---|---|---|
| | | | 7 | 14 | 21 | 30 | 45 | 60 |
| | DMF | | 10 | | | | | |

As is apparent from the above results, adding the amide-type compound (II) to the glycol-type solvent makes it possible to remarkably improve the formulation stability. This is conspicuous for the formulations containing 1–45 wt. % of the amide-type compound, especially for those containing more than 2 wt. % of the same.

This leads to the conclusion that the amount of the amide-type compound in the mixed solvent is preferably about 1 wt. % or more, more preferably about 2 wt. % or more.

For making sure the storage stability of the liquid formulation of the invention, the storage stability test as in the above wa carried out for extended storage periods. The results are shown in Table 2.

TABLE 2

| | No. | MIT | Glycol-type solvent | Compound (II) | storage stability at 50° C. (month) | | |
|---|---|---|---|---|---|---|---|
| | | | | | 2 | 3 | 4 |
| Comparative Example | 1 | 5.0 | EG 95 | DMF 0 | X | X | X |
| Example | 2 | | EG 94 | DMF 1 | △ | X | X |
| | 3 | | EG 93 | DMF 2 | ○ | ○ | △ |
| | 4 | | EG 92 | DMF 3 | ○ | ○ | ○ |
| | 5 | | EG 90 | DMF 5 | ○ | ○ | ○ |
| | 6 | | EG 85 | DMF 10 | ○ | ○ | ○ |
| | 7 | | EG 75 | DMF 20 | ○ | ○ | ○ |
| | 8 | | EG 65 | DMF 30 | ○ | ○ | ○ |
| | 9 | | EG 45 | DMF 50 | ○ | △ | X |
| Comparative | 10 | | EG 25 | DMF 70 | ○ | X | X |
| Example | 11 | | EG 0 | DMF 95 | ○ | X | X |

As is apparent from Table 2, Example Nos. 3–8 containing 2–30 wt. % of the compound (II) relative to 70–98 wt. % of the glycol-type solvent are excellent in long storage stability.

It is estimated that the stability for 4 months at 50° C in this test is substantially equivalent to the stability for more than 8 months at 40° C.

Such a long storage stability offered by the invention permits mass production of the isothiazolone formulation, hence it is especially preferable for reduction in production cost.

For comparison, ethylene glycol monomethyl ether acetate, ethylene glycol dimethyl ether and propylene carbonate disclosed in Japanese Unexamined Patent Publication No. 85271/1990, which are presented herein as Prior Art, were used instead of N,N-dimethylformamide of the compound (II) in the above Examples Nos. 2–9. These formulations for comparison did not exhibit the stability of more than one month. This fact reveals that the combination of the compound (II) with the glycol-type solvent in the present invention is more selective than any other prior-art combinations.

As has been described, the isothiazolone formulation of the invention is far superior to the conventional ones in formulation stability. Further, such a formulation stability is realized without using a metal salt for stabilization, and hence the formulation is free from problems such as emulsion shock due to such a metal salt when used in synthetic polymeric emulsions, thereby contributing to enlarge the use thereof.

It should be understood that Examples recited above are merely examples and are not limitative of the invention.

What is claimed is:

1. A stabilized isothiazolone liquid formulation comprising:

an isothiazolone compound represented by formula (I):

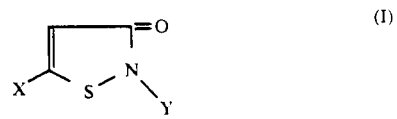

where X represents a hydrogen atom or a halogen atom, and Y represents a lower alkyl group, and a mixed solvent containing 70–98 wt. % of a glycol-type solvent selected from the group consisting of ethylene glycol, diethylene glycol, polyethylene glycol, propylene glycol, dipropylene glycol, tripropylene glycol, polypropylene glycol, ethylene glycol monomethyl ether, ethylene glycol monoethyl ether, ethylene glycol monobutyl ether, diethylene glycol monomethyl ether, diethylene glycol monoethyl ether, tripropylene glycol monomethyl ether, 1,4-butanediol and 1,5-pentanediol and 2–30 wt. % of an amide-type compound represented by formula (II):

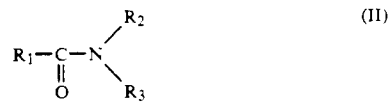

where $R_1$ represents a hydrogen atom or a lower alkyl group, $R_2$ and $R^3$ each represents a lower alkyl group, and $R_1$ may bond to $R_2$ or $R_3$ to form a nitrogen-containing heterocycle, the compound of the formula (I) being dissolved in the mixed solvent in an amount effective to at least dissolve the compound of formula (I).

2. The formulation as set forth in claim 1, wherein the glycol-type solvent is selected from the group consisting of ethylene glycol, diethylene glycol, propylene glycol, dipropylene glycol and 1,4-butanediol.

3. The formulation as set forth in claim 1, wherein the amide-type compound of the formula (II) is selected from the group consisting of N,N-dimethylformamide, N,N-diethylformamide, N,N-dimethylacetamide and N-methyl-2-pyrrolidone.

4. The formulation as set forth in claim 1, wherein the isothiazolone compound of the formula (I) is a mixture of 2-methyl-5-chloro-isothiazolin-3-one and 2-methyl-isothiazolin-3-one.

5. The formulation as set forth in claim 2, wherein the amide-type compound of the formula (II) is selected from the group consisting of N,N-dimethylformamide, N,N-diethylformamide, N,N-dimethylacetamide and N-methyl-2-pyrrolidone.

* * * * *

UNITED STATES PATENT AND TRADEMARK OFFICE
CERTIFICATE OF CORRECTION

PATENT NO. : 5,306,725
DATED : April 26, 1994
INVENTOR(S) : Y. SANO et al.

It is certified that error appears in the above-indentified patent and that said Letters Patent is hereby corrected as shown below:

At column 1, line 20, change "blocidal" to ---biocidal---.
At column 1, line 45, change "nor" to ---or---.
At column 2, line 10, change "3,870,795" to ---3,807,795---.
At column 2, line 25, change "above described" to ---above-described---.
At column 2, line 34, delete "the fact to reach".
At column 2, line 35, delete "the present invention".
At column 2, line 36, before "amide-type solvent" insert ---The amide-type compound (II) is well known as an---.
At column 2, line 64, change "where $R_{10}$" to ---(where $R_1$---.

At column 3, line 22, delete ". Such a".
At column 6, Table 1, Comparative Example, No. 10, column day 14, change "O" to ---X---.
At column 6, Table 1, Comparative Example No. 11, column day 14, change "O" to ---X---.

UNITED STATES PATENT AND TRADEMARK OFFICE
CERTIFICATE OF CORRECTION

PATENT NO. : 5,306,725
DATED : April 26, 1994
INVENTOR(S) : Y. SANO et al.

It is certified that error appears in the above-indentified patent and that said Letters Patent is hereby corrected as shown below:

At column 7, line 22, change "wa" to ---was---.
At column 7, lines 42 and 43, change "3-8con-taining" to ---3-8 containing---.
At column 7, line 58, change "Examples" to ---Example---.

Signed and Sealed this

Eleventh Day of February, 1997

Attest:

BRUCE LEHMAN

Attesting Officer          Commissioner of Patents and Trademarks